(12) United States Patent
Rotman et al.

(10) Patent No.: US 12,349,991 B2
(45) Date of Patent: Jul. 8, 2025

(54) AUTOMATIC ROBOTIC PROCEDURE FOR SKIN CUTTING, TISSUE PATHWAY, AND DILATION CREATION

(71) Applicant: Mazor Robotics Ltd., Caesarea (IL)

(72) Inventors: Elad Rotman, Netanya (IL); Eitan Detinis, Shefayim (IL); Ido Zucker, Tel Aviv (IL); Eliyahu Zehavi, Tel Aviv (IL); Yonatan Ushpizin, Glil Yam (IL)

(73) Assignee: Mazor Robotics Ltd., Caesarea (IL)

( * ) Notice: Subject to any disclaimer, the term of this patent is extended or adjusted under 35 U.S.C. 154(b) by 759 days.

(21) Appl. No.: 17/590,979

(22) Filed: Feb. 2, 2022

(65) Prior Publication Data
US 2023/0240766 A1    Aug. 3, 2023

(51) Int. Cl.
*A61B 34/30* (2016.01)
*A61B 17/3209* (2006.01)
(Continued)

(52) U.S. Cl.
CPC ........ *A61B 34/30* (2016.02); *A61B 17/32093* (2013.01); *A61B 17/3417* (2013.01);
(Continued)

(58) Field of Classification Search
CPC .......... A61B 17/32093; A61B 17/3417; A61B 17/3496; A61B 2017/3456;
(Continued)

(56) References Cited

U.S. PATENT DOCUMENTS 6,155,768 A * 12/2000 Bacchi ............. H01L 21/68707
414/416.03
6,645,196 B1    11/2003 Nixon et al.
(Continued)

FOREIGN PATENT DOCUMENTS

JP    2006/305717    11/2006
WO   WO 2020/195208   10/2020
(Continued)

OTHER PUBLICATIONS

International Search Report and Written Opinion for International (PCT) Patent Application No. PCT/IL2023/050063, dated Apr. 19, 2023, 12 pages.
(Continued)

*Primary Examiner* — Kathleen S Holwerda
*Assistant Examiner* — Daniel Icet
(74) *Attorney, Agent, or Firm* — Sheridan Ross P.C.

(57) ABSTRACT

A robotic surgical system according to at least one embodiment of the present disclosure includes a robot arm including a proximal end and a distal end and a surgical tool that attaches to the distal end of the robot arm via a robot mount flange on the surgical tool. The surgical tool includes a blade support tip that extends from a first end and a rod that extends from a second end opposite the first end. The rod may include a blunt tip end and an actuation end, where the blunt tip end extends from the second end. Accordingly, the surgical tool may be rotatable about a tool rotation axis between a cutting position disposing the blade support tip in proximity to a target site and a tissue pathway creation position disposing the blunt tip end in proximity to the target site.

20 Claims, 14 Drawing Sheets

(51) Int. Cl.
    *A61B 17/34*     (2006.01)
    *A61B 34/00*     (2016.01)
    *A61B 34/20*     (2016.01)
    *A61B 90/00*     (2016.01)

(52) U.S. Cl.
    CPC .......... *A61B 17/3496* (2013.01); *A61B 34/25* (2016.02); *A61B 2017/3456* (2013.01); *A61B 34/20* (2016.02); *A61B 2090/062* (2016.02); *A61B 2090/064* (2016.02)

(58) Field of Classification Search
    CPC ........ A61B 2090/062; A61B 2090/064; A61B 90/10; A61B 90/11; A61B 17/295; A61B 90/50; A61B 2017/320044; A61B 34/30–77; A61M 29/00
    See application file for complete search history.

(56) References Cited

U.S. PATENT DOCUMENTS

| | | | |
|---|---|---|---|
| 9,161,760 | B2 | 10/2015 | Suarez et al. |
| 10,441,371 | B2 | 10/2019 | Hendrick et al. |
| 2002/0102156 | A1* | 8/2002 | Woodruff .................. B25J 5/02 414/744.5 |
| 2013/0144274 | A1* | 6/2013 | Stefanchik ............. A61B 34/71 606/1 |
| 2013/0172903 | A1* | 7/2013 | Suarez ................... A61B 34/30 606/1 |
| 2020/0170667 | A1 | 6/2020 | Kiev |
| 2021/0059718 | A1 | 3/2021 | Karam |
| 2021/0146554 | A1* | 5/2021 | Hudgens ........... H01L 21/67754 |
| 2022/0009083 | A1* | 1/2022 | Hosek ...................... B25J 18/00 |
| 2022/0192769 | A1* | 6/2022 | Conus .................. A61B 17/068 |
| 2023/0092748 | A1* | 3/2023 | Bagheri Ghavifekr ...................... A61B 34/37 606/1 |
| 2024/0050173 | A1* | 2/2024 | Wilson ................... A61B 90/30 |

FOREIGN PATENT DOCUMENTS

| | | |
|---|---|---|
| WO | WO 2021/171154 | 9/2021 |
| WO | WO 2021/255672 | 12/2021 |

OTHER PUBLICATIONS

U.S. Appl. No. 17/591,004, filed Feb. 2, 2022, Rotman et al.

\* cited by examiner

US 12,349,991 B2

AUTOMATIC ROBOTIC PROCEDURE FOR SKIN CUTTING, TISSUE PATHWAY, AND DILATION CREATION

BACKGROUND

The present disclosure is generally directed to surgical systems and relates more particularly to robotic surgical devices.

Surgical robots may assist a surgeon or other medical provider in carrying out a surgical procedure or may complete one or more surgical procedures autonomously. Providing controllable linked articulating members allows a surgical robot to reach areas of a patient anatomy during various medical procedures.

BRIEF SUMMARY

Example aspects of the present disclosure include:

A robotic surgical system, comprising: a robot arm comprising a proximal end and a distal end; and a surgical tool, comprising: a housing comprising a longitudinal axis extending from a first end of the housing to a second end of the housing; a blade support tip extending from the first end of the housing in a direction away from the second end of the housing along the longitudinal axis; a blade disposed at least partially within the blade support tip, the blade comprising a sharpened edge; a rod comprising a blunt tip end and an actuation end, wherein the actuation end is disposed within the housing, and wherein the blunt tip end extends from the second end of the housing in a direction away from the first end of the housing along the longitudinal axis; and a robot interface bracket coupled to the housing, the robot interface bracket comprising a robot mount flange comprising a tool rotation axis arranged perpendicular to the longitudinal axis, wherein the surgical tool is attached to the distal end of the robot arm via the robot mount flange, wherein the surgical tool is rotatable about the tool rotation axis between a cutting position disposing the blade support tip in proximity to a target site and a tissue pathway creation position disposing the blunt tip end in proximity to the target site.

Any of the aspects herein, wherein the blade is moveable between a retracted state where the sharpened edge is concealed within the blade support tip and an extended state where the sharpened edge is exposed from the blade support tip.

Any of the aspects herein, further comprising a tube that is moved along the rod when the surgical tool is in the tissue pathway creation position, wherein the tube dilates a pathway from the target site to an internal point of the target site.

Any of the aspects herein, further comprising one or more motors disposed within the housing that control extension of the blunt tip end of the rod from the second end of the housing in the direction away from the first end of the housing along the longitudinal axis.

Any of the aspects herein, further comprising a depth sensing subsystem disposed within the housing, the depth sensing subsystem comprising one or more encoder sensors that indicate one or more characteristics of the surgical tool.

Any of the aspects herein, wherein the depth sensing subsystem is used to control and sense the depth of insertion for the blade disposed at least partially within the blade support tip in the cutting position, for the blunt tip end of the rod in the tissue pathway creation position, or a combination thereof.

Any of the aspects herein, wherein the depth sensing subsystem further comprises one or more encoder magnets, one or more static nuts, or a combination thereof for sensing the depth of insertion of the surgical tool.

Any of the aspects herein, wherein the one or more characteristics of the surgical tool indicated by the one or more encoder sensors comprise a depth of insertion of the surgical tool between the target site and an internal point of the target site, a position of the surgical tool, a velocity of the surgical tool, or a combination thereof.

Any of the aspects herein, further comprising an axial force sensing subsystem disposed within the housing, the axial force sensing subsystem comprising one or more force sensors for sensing a pressure exerted by the surgical tool, for sensing an amount of resistance encountered by the surgical tool, or a combination thereof.

Any of the aspects herein, wherein the amount of resistance sensed by the axial force sensing subsystem indicates a presence of a tissue layer.

Any of the aspects herein, wherein the surgical tool comprises a sterilizable unit.

A surgical tool, comprising: a housing comprising a longitudinal axis extending from a first end of the housing to a second end of the housing; a blade support tip extending from the first end of the housing in a direction away from the second end of the housing along the longitudinal axis; a blade disposed at least partially within the blade support tip, the blade comprising a sharpened edge; a rod comprising a blunt tip end and an actuation end, wherein the actuation end is disposed within the housing, and wherein the blunt tip end extends from the second end of the housing in a direction away from the first end of the housing along the longitudinal axis; and a robot interface bracket coupled to the housing, the robot interface bracket comprising a robot mount flange comprising a tool rotation axis arranged perpendicular to the longitudinal axis, wherein the surgical tool is attached to a distal end of a robot arm via the robot mount flange, wherein the surgical tool is rotatable about the tool rotation axis between a cutting position disposing the blade support tip in proximity to a target site and a tissue pathway creation position disposing the blunt tip end in proximity to the target site.

Any of the aspects herein, wherein the blade is moveable between a retracted state where the sharpened edge is concealed within the blade support tip and an extended state where the sharpened edge is exposed from the blade support tip.

Any of the aspects herein, further comprising a tube that is moved along the rod when the surgical tool is in the tissue pathway creation position, wherein the tube dilates a pathway from the target site to an internal point of the target site.

Any of the aspects herein, further comprising one or more motors disposed within the housing that control extension of the blunt tip end of the rod from the second end of the housing in the direction away from the first end of the housing along the longitudinal axis.

Any of the aspects herein, further comprising a depth sensing subsystem disposed within the housing, the depth sensing subsystem comprising one or more encoder sensors that indicate one or more characteristics of the surgical tool.

Any of the aspects herein, wherein the depth sensing subsystem is used to control and sense the depth of insertion for the blade disposed at least partially within the blade support tip in the cutting position, for the blunt tip end of the rod in the tissue pathway creation position, or a combination thereof.

Any of the aspects herein, wherein the depth sensing subsystem further comprises one or more encoder magnets, one or more static nuts, or a combination thereof for sensing the depth of insertion of the surgical tool.

Any of the aspects herein, further comprising an axial force sensing subsystem disposed within the housing, the axial force sensing subsystem comprising one or more force sensors for sensing a pressure exerted by the surgical tool, for sensing an amount of resistance encountered by the surgical tool, or a combination thereof.

A system, comprising: a surgical robot comprising: a robot arm comprising a proximal end and a distal end; and a surgical tool, comprising: a housing comprising a longitudinal axis extending from a first end of the housing to a second end of the housing; a blade support tip extending from the first end of the housing in a direction away from the second end of the housing along the longitudinal axis; a blade disposed at least partially within the blade support tip, the blade comprising a sharpened edge; a rod comprising a blunt tip end and an actuation end, wherein the actuation end is disposed within the housing, and wherein the blunt tip end extends from the second end of the housing in a direction away from the first end of the housing along the longitudinal axis; and a robot interface bracket coupled to the housing, the robot interface bracket comprising a robot mount flange comprising a tool rotation axis arranged perpendicular to the longitudinal axis, wherein the surgical tool is attached to the distal end of the robot arm via the robot mount flange; and a processor coupled with the surgical robot; and a memory coupled with and readable by the processor and storing therein instructions that, when executed by the processor, cause the processor to: determine a first position for the surgical tool, wherein the surgical tool is rotatable and wherein the first position comprises a cutting position that disposes the blade support tip in proximity to a target site or a tissue pathway creation position that disposes the blunt tip end in proximity to the target site; and rotate the surgical tool about the tool rotation axis to the first position.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
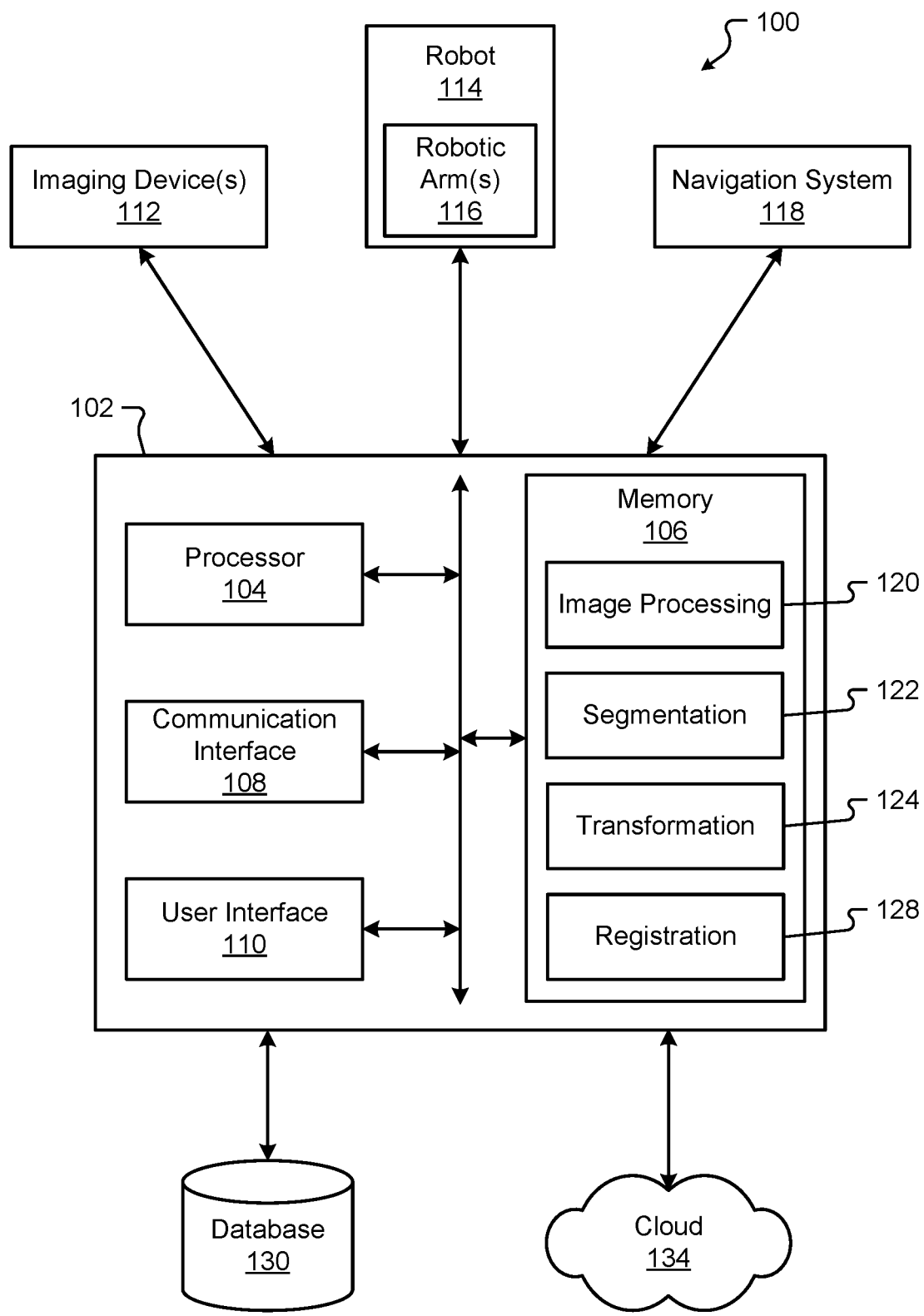
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system and further from the region of surgical interest in or on the patient, and distal being closer to the region of surgical interest in or on the patient and further from the operator or user of the system.

During minimal invasive surgeries, a physician or surgeon may be unable to see a selected vertebra section to be reached through the body that is a target for the minimal invasive surgeries. Typically, the physician or surgeon usually makes a sensible guess by pressing on the skin of a patient and performs manual skin cutting, tissue pathway creation, and pathway dilation. However, this guesswork can cause tissue harm if the pathway trajectory is not pointing to the desired vertebrae section (e.g., a pedicle) and prolong procedure time.

Additionally, the physician or surgeon may need to make a precise length incision on the patient to allow for insertion of a trocar for tissue pathway creation and/or pathway dilation for a surgery. For example, a trocar of diameter, D, requires an incision of length, L, where $L=\pi \times D/2$ (e.g., a required skin incision length can be reduced to ~1.4×max tool diameter). If the surgeon makes the incision too short, dangerous force may be required to place the trocar as the skin is forced open around the trocar shaft, leading to injury of the organs below. Additionally, the extra shear may also crush skin edges, leading to imperfect closures of the incision that are more prone to failure and infection. Conversely, incisions that are too large will leave the trocars too loose, such that the trocars may slide in and out of an incision site during the surgery, leading to decreased precision and delays as the trocars are constantly repositioned.

As described herein, to avoid these potential issues (e.g., causing tissue harm, prolonging procedure time, improperly making an incision, etc.), a surgical tool is provided that can attach to a robotic arm in a robotic surgery system, where the surgical tool includes a blade for cutting skin/fat/fascia and a blunt tip trocar with a dilator for creating a highly accurate pathway through the tissue to the selected vertebra. The surgical tool can rotate about a rotational axis to produce the blade or the blunt tip trocar with the dilator depending on which side is needed to perform a corresponding step of a surgical procedure. That is, the surgical tool includes two (2) parts that the surgical tool can rotate between: a first part that includes the blade for skin cutting (e.g., that can also cut other tissue layers, such as fat and fascia) and a second part that includes the blunt tip trocar with the dilator (e.g., a trocar blunt) for creating a tissue pathway and a dilator for pathway dilation.

Accordingly, this surgical tool can create a high accuracy pathway (e.g., for a minimal invasive surgery) from patient skin level to a selected vertebrae section (e.g., according to computerized tomography (CT) images taken prior to the procedure). Additionally, this surgical tool can support both manual procedures and robotic procedures. For example, the robotic procedures for which the surgical tool can support may include, and is not limited to, inserting screws in a patient (e.g., into a pedicle) through a created skin incision and tissue pathway, inserting a cage in a patient (e.g., to a vertebra disc space) through the created pathway, inserting a drill for decompression through the created pathway, etc.

The surgical tool described and provided herein is designed to perform a clean skin cut of a minimum possible length (e.g., skin should be in tension in order to create the clean cut), dilate a channel (e.g., tissue pathway and dilation creation) from skin surface to a target area inside a patient (e.g., to bone), have a maximum first insertion blunt diameter (e.g., eight (8) millimeters (mm)), have a maximum penetration from skin surface to the target area (e.g., 140 mm), allow a maximum allowed axial force (e.g., six (6) kilograms (kg) of force), and support a maximum operation time from an initial skin cut to dilator exit (e.g., 80 seconds). Additionally, the surgical tool may be able to rotate about a rotational axis, which reduces a required axial force for insertion of either part of the surgical tool (e.g., blade or trocar). The trocar of the surgical tool may also include a helix feature or construction that reduces the required axial force for insertion. The surgical tool also allows for puncturing fascia or other tissue layers by a sharp edge (e.g., the blade part). Accordingly, the surgical tool provides or supports skin incision operations, as well as channel dilation preparation (e.g., tissue pathway and dilation creation) for inserting drills or other minimally invasive surgery (MIS) tools into a patient.

In some examples, the surgical tool may also include one or more sensors for performing different measurements to assist in operations or procedures performed using the surgical tool. For example, the sensors may sense current axial forces while cutting and inserting the trocar and dilator to make sure the surgical tool is being operated under reasonable loads and to find high resistance areas (e.g., such as fascia) that may require momentary blade use. Additionally, the sensors may be used for sensing a skin surface depth. For example, as the skin sags during initial cut and maybe also when dilating, the sensors may control and sense the depth of insertion from the skin surface to prevent from inserting either end of the surgical tool too far into the patient and potentially causing harm to the patient. In some examples, the sensors may include or be connected to encoders that will measure directly the position of different stages for insertion of the surgical tool. Such sensors may be referred to or considered encoder sensors. Additionally or alternatively, these sensors may give information about a position and a velocity of the surgical tool. Different driving methods and mechanisms (e.g., tool motors) may be employed within the surgical tool to control extension and insertion of the surgical tool. Additionally, in some examples, the surgical tool may be sterilizable and/or disposable.

Embodiments of the present disclosure provide technical solutions to one or more of the problems of (1) causing unnecessary tissue harm during surgeries, (2) prolonging procedure times for the surgeries, and (3) making improperly sized incisions. In one example, the technical solutions may include using the surgical tool described and provided herein to more efficiently perform surgeries. A robotic surgical system that includes the surgical tool and the method of combining a cutting blade and a blunt tip trocar in a single tool that can be rotated between operative positions allows for the creation of a highly accurate pathway from an incision site to a select vertebra section (e.g., according to CT images taken prior to a procedure). By creating an optimal path between the incision made by a cutting tool (e.g., the blade) and a pathway made by a blunt trocar (e.g., the blunt tip), the amount of tissue displaced is minimized, the length of the pathway is controlled along a direct route, and patient recovery is improved. Moreover, this combined surgical tool described herein allows the pathway to be created immediately after the incision is made, thereby reducing the amount of time for the procedure. The combined surgical tool may also support making a more precisely sized incision for inserting and using the blunt trocar tip to create the tissue pathway and dilation to reduce the risk of making the incision too small or too large.

Turning first to FIG. 1, a block diagram of a system 100 according to at least one embodiment of the present disclosure is shown. The system 100 may be used to operate a robot 114 and a surgical tool attached to a robotic arm 116 of the robot 114, where the surgical tool includes both a blade for cutting different tissue layers (e.g., skin, fat, fascia, etc.) and a blunt tip trocar with a dilator for creating a highly accurate pathway through the tissue layers to a target site of a patient (e.g., a selected vertebra). In some examples, the system 100 may control, pose, and/or otherwise manipulate a surgical mount system, a surgical arm, and/or surgical tools attached thereto and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or may comprise RAM, DRAM, SDRAM, other solid-state memory, any memory described herein, or any other tangible, non-transitory memory for storing computer-readable data and/or instructions. The memory 106 may store information or data useful for completing, for example, any step of the method 800 described herein, or of any other methods. The memory 106 may store, for example, instructions and/or machine learning models that support one or more functions of the robot 114.

For instance, the memory 106 may store content (e.g., instructions and/or machine learning models) that, when executed by the processor 104, enable image processing 120, segmentation 122, transformation 124, and/or registration 128. Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or may comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate to one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or may comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or the robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, e.g., pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or may comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the method 800 described herein. The system 100 or similar systems may also be used for other purposes.

Figure 2A:
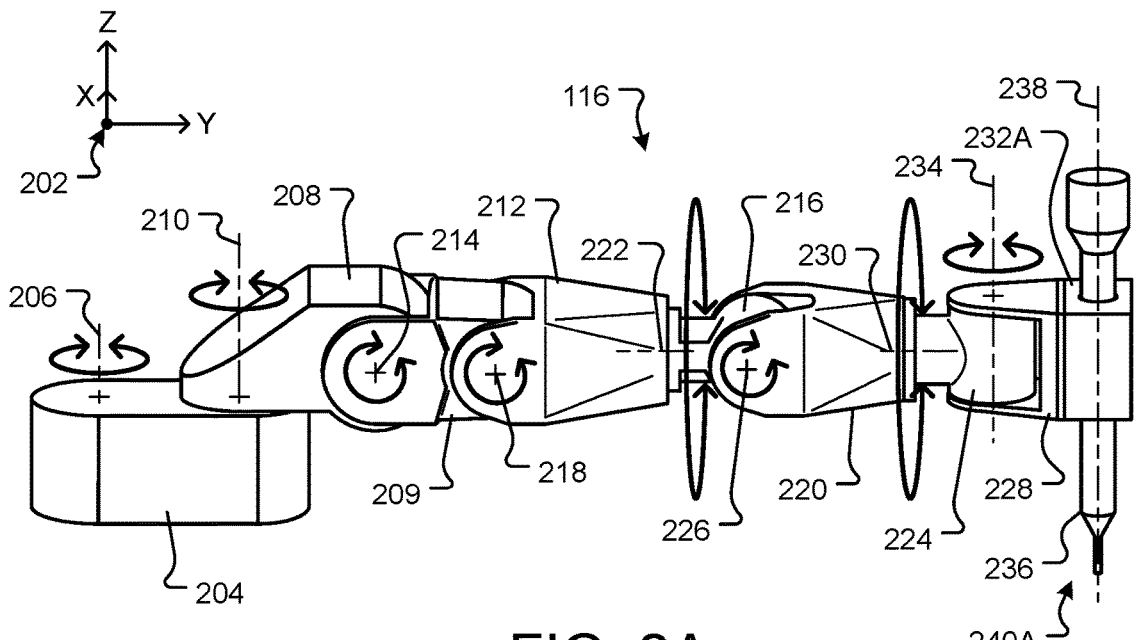
FIG. 2A is a perspective diagram of a robotic surgical system according to at least one embodiment of the present disclosure.
Figure 2B:
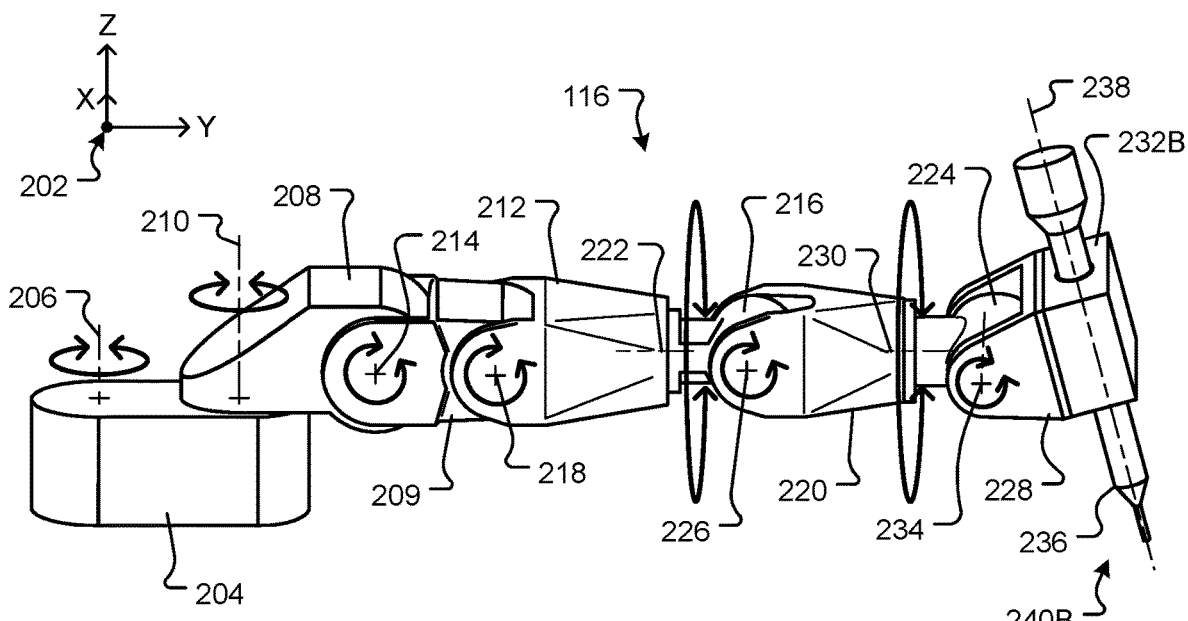
FIG. 2B is a perspective diagram of a robotic surgical system according to at least one embodiment of the present disclosure.

Referring now to FIGS. 2A and 2B, perspective diagrams of a robotic surgical system with different end effector 240A, 240B mount positions are shown in accordance with examples of the present disclosure. More specifically, FIGS. 2A and 2B show the robotic arm 116 of the robot 114 connected to an end effector 240A, 240B holding a surgical tool 236. As described herein, the surgical tool 236 may be a single surgical tool capable of cutting different tissue layers (e.g., skin, fat, fascia, etc.) using a blade end of the surgical tool 236 (e.g., a first end) and of creating a highly accurate pathway through the tissue layers to a target site of a patient (e.g., a selected vertebra) using a rod with a blunt tip end of the surgical tool 236 (e.g., a blunt end trocar with a dilator), where the surgical tool 236 is rotatable around a rotational axis to position an appropriate end of the surgical tool 236 to perform a corresponding action (e.g., for cutting or for creating a tissue pathway and/or dilation).

Additionally or alternatively, the surgical tool 236 may correspond to different surgical tools used between operations in a surgical application. For instance, a first surgical tool 236 may include a direction-specific blade that may require a specific rotational alignment and placement in the tool block 232A, 232B, while another surgical tool 236 may include a unidirectional cutting tool that is independent of rotational alignment in the tool block 232A, 232B.

Features of the robot 114 and/or robotic arm 116 may be described in conjunction with a coordinate system 202. The coordinate system 202, as shown in FIGS. 2A and 2B, includes three-dimensions comprising an X-axis, a Y-axis, and a Z-axis. Additionally or alternatively, the coordinate system 202 may be used to define planes (e.g., the XY-plane, the XZ-plane, and the YZ-plane) of the robot 114 and/or robotic arm 116. These planes may be disposed orthogonal, or at 90 degrees, to one another. While the origin of the coordinate system 202 may be placed at any point on or near the components of the robot 114, for the purposes of description, the axes of the coordinate system 202 are always disposed along the same directions from figure to figure, whether the coordinate system 202 is shown or not. In some examples, reference may be made to dimensions, angles, directions, relative positions, and/or movements associated with one or more components of the robot 114 and/or robotic arm 116 with respect to the coordinate system 202. For example, the width of the robotic arm 116 (e.g., running from the side shown in the foreground to the side in the background, into the page) may be defined as a dimension along the X-axis of the coordinate system 202, the height of the robotic arm 116 may be defined as a dimension along the Z-axis of the coordinate system 202, and the length of the robotic arm 116 (e.g., running from a proximal end at the first link 204 to a distal end at the seventh link 224, etc.) may be defined as a dimension along the Y-axis of the coordinate system 202. Additionally or alternatively, the height of the system 100 may be defined as a dimension along the Z-axis of the coordinate system 202, a reach of the robotic arm 116 may be defined as a dimension along the Y-axis of the coordinate system 202, and a working area of the robotic arm 116 may be defined in the XY-plane with reference to the corresponding axes of the coordinate system 202.

The robotic arm 116 may be comprised of a number of links 204, 208, 209, 212, 216, 220, 224 that interconnect with one another at respective axes of rotation 206, 210, 214, 218, 222, 226, 230, 234, or joints. There may be more or fewer links 204, 208, 209, 212, 216, 220, 224 and/or axes of rotation 206, 210, 214, 218, 222, 226, 230, 234 than are shown in FIGS. 2A and 2B. In any event, the robotic arm 116 may have a first link 204 disposed at a proximal end of the robotic arm 116 and an end mount flange 228 disposed furthest from the proximal end at a distal end of the robotic arm 116. The first link 204 may correspond to a base of the robotic arm 116. In some examples, the first link 204 may rotate about first rotation axis 206. A second link 208 may be connected to the first link 204 at a second rotation axis 210, or joint. The second link 208 may rotate about the second rotation axis 210. In one example, the first rotation axis 206 and the second rotation axis 210 may be arranged parallel to one another. For instance, the first rotation axis 206 and the second rotation axis 210 are shown extending along the Z-axis in a direction perpendicular to the XY-plane.

The robotic arm 116 may comprise a third link 209 that is rotationally interconnected to the second link 208 via the third rotation axis 214, or joint. The third rotation axis 214 is shown extending along the X-axis, or perpendicular to the first rotation axis 206 and second rotation axis 210. In this position, when the third link 209 is caused to move (e.g., rotate relative to the second link 208), the third link 209 (and the components of the robotic arm 116 extending from the third link 209) may be caused to move into or out of the XY-plane. The fourth link 212 is shown rotationally interconnected to the third link 209 via the fourth rotation axis 218, or joint. The fourth rotation axis 218 is arranged parallel to the third rotation axis 214. The fourth rotation axis 218 extends along the X-axis allowing rotation of the fourth link 212 into and out of the XY-plane.

In some examples, the robotic arm 116 may comprise one or more wrists 216, 224. The fifth link 216, or wrist, is shown rotationally interconnected to the fourth link 212 via a fifth rotation axis 222, or wrist joint. The fifth rotation axis 222 is shown extending along the Y-axis, which is perpendicular to the X-axis and the Z-axis. During operation of the robot 114, causing the fifth link 216 to rotate about the fifth rotation axis 222 may cause the components of the robotic arm 116 distal the joint at the fifth rotation axis 222 (e.g., the fifth link 216, the sixth link 220, the seventh link 224, the end mount flange 228, and the end effector 240A, 240B, etc.) to rotate about the Y-axis.

The sixth link 220 is rotationally interconnected to the fifth link 216 via the sixth rotation axis 226. The sixth rotation axis 226 extends along the X-axis and provides for rotation of the sixth link 220 relative to the fifth link 216 (e.g., into and out of the XY-plane in the position shown).

The seventh link 224, or wrist, is shown rotationally interconnected to the sixth link 220 via a seventh rotation axis 230, or wrist joint. The seventh rotation axis 230 is shown extending along the Y-axis (e.g., perpendicular to the X-axis and the Z-axis). During operation of the robot 114, causing the seventh link 224 to rotate about the seventh rotation axis 230 may cause the components of the robotic arm 116 distal the joint at the seventh rotation axis 230 (e.g., the end mount flange 228, and the end effector 240A, 240B, etc.) to rotate about the Y-axis.

Located at the distal end of the robotic arm 116, an end mount flange 228 may be rotationally interconnected to the end mount flange 228 via an eighth, or mount flange rotation, axis 234. In FIG. 2A, the seventh link 224 is positioned rotationally about the seventh rotation axis 230 such that the end mount flange 228 is oriented where the mount flange rotation axis 234 is extending along the Z-axis. In FIG. 2B, the seventh link 224 is positioned rotationally about the seventh rotation axis 230 such that the end mount flange 228 is oriented where the mount flange rotation axis 234 is extending along the X-axis. In some examples, at least the seventh link 224 may be rotated about the seventh rotation axis 230 to move between the end mount flange 228 position shown in FIG. 2A and the end mount flange 228 position shown in FIG. 2B, or vice versa. The end mount flange 228 and the mount flange rotation axis 234 may be the last movable (e.g., motor actuated, etc.) link and joint of the robotic arm 116. Moving between these two positions of the end mount flange 228 allows a particular end effector 240A, 240B to be attached and manipulated, or operated, according to a corresponding movement profile (e.g., range and limits) or set of kinematic solutions for the robot 114 (e.g., the robotic arm 116 and the surgical tool 236, etc.).

FIG. 2A shows first movement kinematics for the robotic arm 116 when the first tool block 232A of the first end effector 240A disposes the surgical tool axis 238 parallel to the mount flange rotation axis 234. In the position shown in FIG. 2A, rotation into and/or out of the XY-plane between the seventh link 224 and the first end effector 240A is prevented. This position and arrangement may be ideal for applications (e.g., operations, procedures, etc.) where an end rotational position of the surgical tool 236 may need to be maintained for the robotic arm 116. For example, the surgical tool 236 in the first end effector 240A may correspond to an imaging device that may need to be maintained in a particular nonrotational position relative to a patient during imaging (e.g., where an imaging plane of the surgical tool 236 should be maintained parallel to the XY-plane as other joints of the robotic arm 116 move the distal end closer to or further from the proximal end). In this case, the corresponding arrangement of the surgical tool axis 238 (e.g., parallel to the mount flange rotation axis 234) associated with the first end effector 240A may be preferred. In another example, rotation of the surgical tool 236 into, or out of, the XY-plane may need to be prevented to ensure accuracy of movement along the Y-axis, in the XY-plane, and/or the like. Additionally or alternatively, a distance between a reference plane and an end of the surgical tool 236 (e.g., along the Z-axis) may need to remain constant during operation of the robot 114. In any of these cases, the position and arrangement shown in conjunction with FIG. 2A (e.g., preventing end rotation relative to the XY-plane) may be preferred.

FIG. 2B shows second movement kinematics for the robotic arm 116 when the second tool block 232B of the second end effector 240B disposes the surgical tool axis 238 perpendicular (e.g., at 90 degrees) to the mount flange rotation axis 234. In this alternative position, the end mount flange 228 and second end effector 240B may be allowed to rotate relative to the seventh link 224. Stated another way, in this alternative position, the end mount flange 228 and second end effector 240B may be allowed to rotate into and/or out of the XY-plane (e.g., relative to seventh link 224 at the mount flange rotation axis 234). This position and arrangement may be ideal when a precise rotational movement of the surgical tool 236 at the distal end of the robotic arm 116 is desired. In contrast to the position and arrangement shown in FIG. 2A, where the closest rotation of the first end effector 240A about the X-axis is provided at the sixth rotation axis 226, the position and arrangement of FIG. 2B allows the second end effector 240B to be rotated about the X-axis about the mount flange rotation axis 234. Among other things, this position and arrangement may be used for any application where a movement of the second end effector 240B including an end rotation into and/or out of the XY-plane is desired for the surgical tool 236. Such applications may include directional cutting operations, probing movements, displacement of tissue and organs, and/or other surgical operations.

Figure 3A:
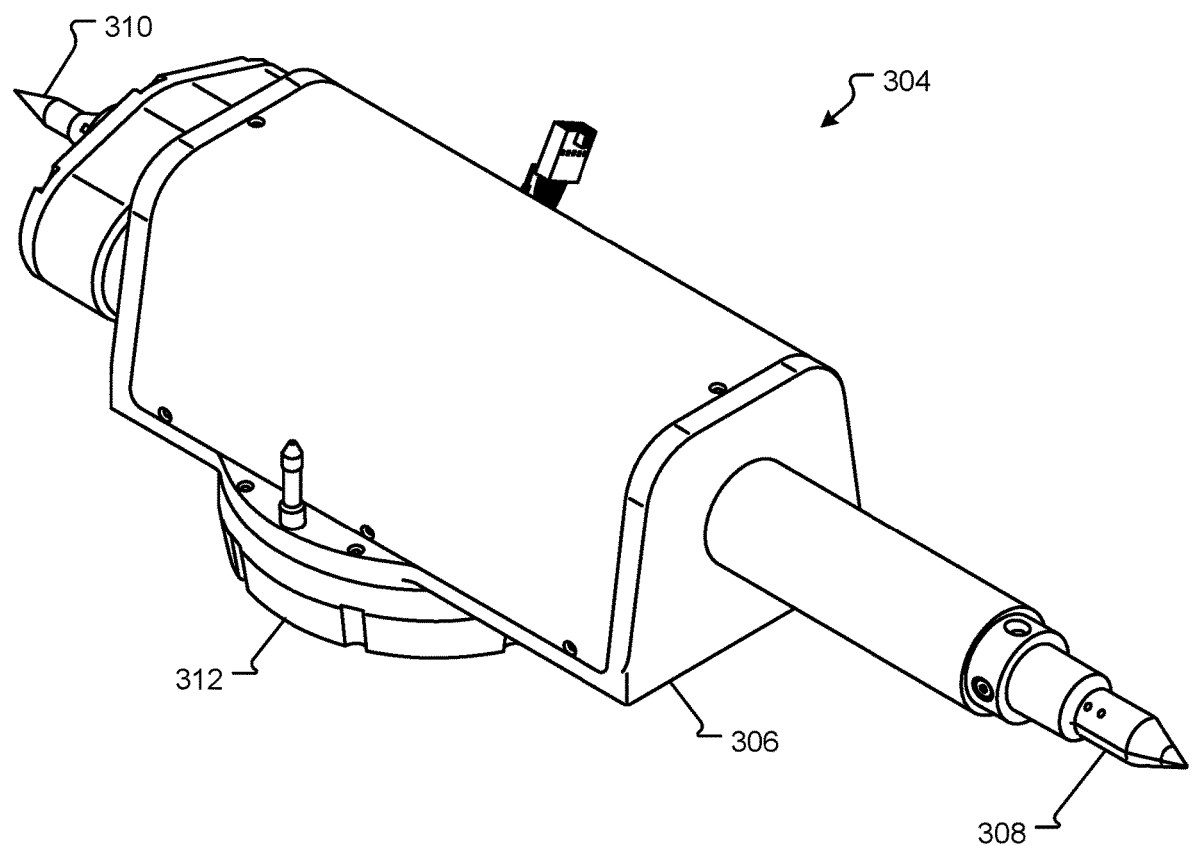
FIG. 3A is a perspective diagram of a surgical tool according to at least one embodiment of the present disclosure.

FIG. 3A shows a perspective diagram 300 of a surgical tool 304 according to at least one embodiment of the present disclosure. As illustrated in FIG. 3A and as described herein, the surgical tool 304 may include a housing 306, a blade support tip 308 extending from a first end of the housing 306, a rod 310 (e.g., a trocar) that extends from a second end of the housing 306 in a direction away from the first end of the housing 306, and a robot interface bracket 312 that is coupled to the housing 306. The blade support tip 308 may include a blade that is disposed at least partially within the blade support tip 308, where the blade includes a sharpened edge. The blade may be moveable between a retracted stage where the sharpened edge is concealed within the blade support tip 308 and an extended state where the sharpened edge is exposed from the blade support tip 308. The rod 310 may include a blunt tip end and an actuation end, where the actuation end is disposed within the housing 306 and where the blunt tip end extends from the second end of the housing 306. The blade of the blade support tip 308 and the blunt tip end and actuation end of the rod 310 are described in greater detail with reference to FIGS. 4A-4B.

Figure 3B:
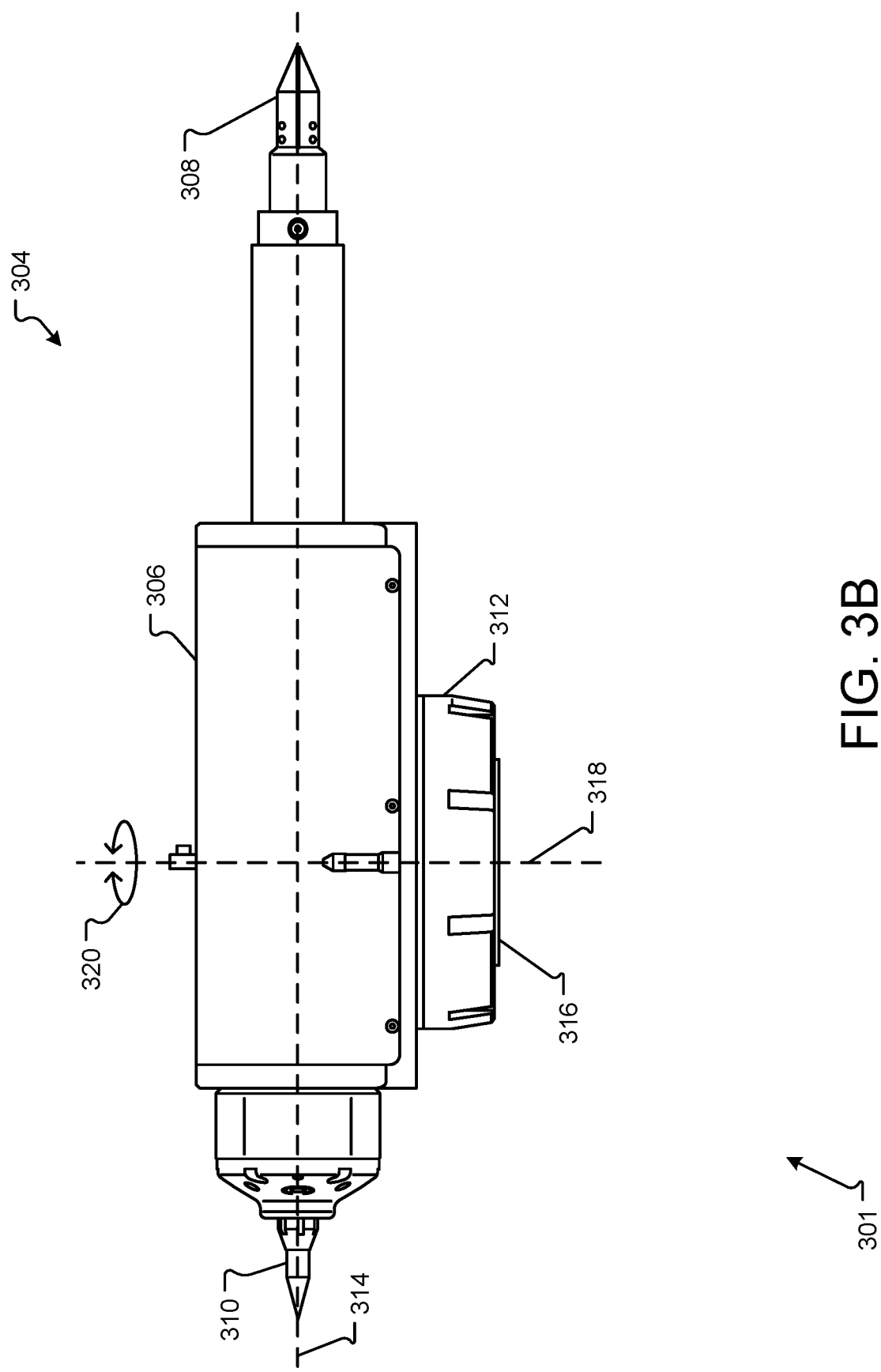
FIG. 3B is a side view diagram of the surgical tool according to at least one embodiment of the present disclosure.

FIG. 3B shows a side view diagram 301 of the surgical tool 304 according to at least one embodiment of the present disclosure. As illustrated in FIG. 3B, the housing 306 may include a longitudinal axis 314 that extends from the first end of the housing 306 (e.g., from which the blade support tip 308 extends) to the second end of the housing 306 (e.g., from which the rod 310 extends). Accordingly, the blade support tip 308 extends from the first end of the housing 306 in a direction away from the second end of the housing 306 along the longitudinal axis 314, and the blunt tip end of the rod 310 extends from the second end of the housing 306 in a direction away from the first end of the housing 306 along the longitudinal axis 314.

Additionally, the robot interface bracket 312 coupled to the housing 306 may include a robot mount flange 316 that further includes a tool rotation axis 318 arranged perpendicular to the longitudinal axis 314. The surgical tool 304 can attach to a distal end of a robot arm (e.g., a robot arm 116 of a robot 114 or a robotic surgical system) via the robot mount flange 316 (e.g., by attaching to an end mount flange of the robot arm as described with reference to FIGS. 2A and 2B). In some examples, the surgical tool 304 may be able to perform a rotation 320 about the tool rotation axis 318 (e.g., the surgical tool 304 is rotatable). With the rotation 320, the surgical tool 304 can rotate between a cutting position disposing the blade support tip 308 in proximity to a target site and a tissue pathway creation position disposing the blunt tip end of the rod 310 in proximity to the target site. That is the surgical tool 304 can rotate between presenting the blade support tip 308 at the target site (e.g., for cutting skin, fascia, fat, etc.) and presenting or extending the blunt tip end of the rod 310 at the target site (e.g., for tissue pathway creation and/or dilation creation) without having to change out the surgical tool 304 to perform individual steps of a surgical operation.

In some examples, the surgical tool 304 may include one or more motors for performing or enabling the rotation 320.

Figure 3C:
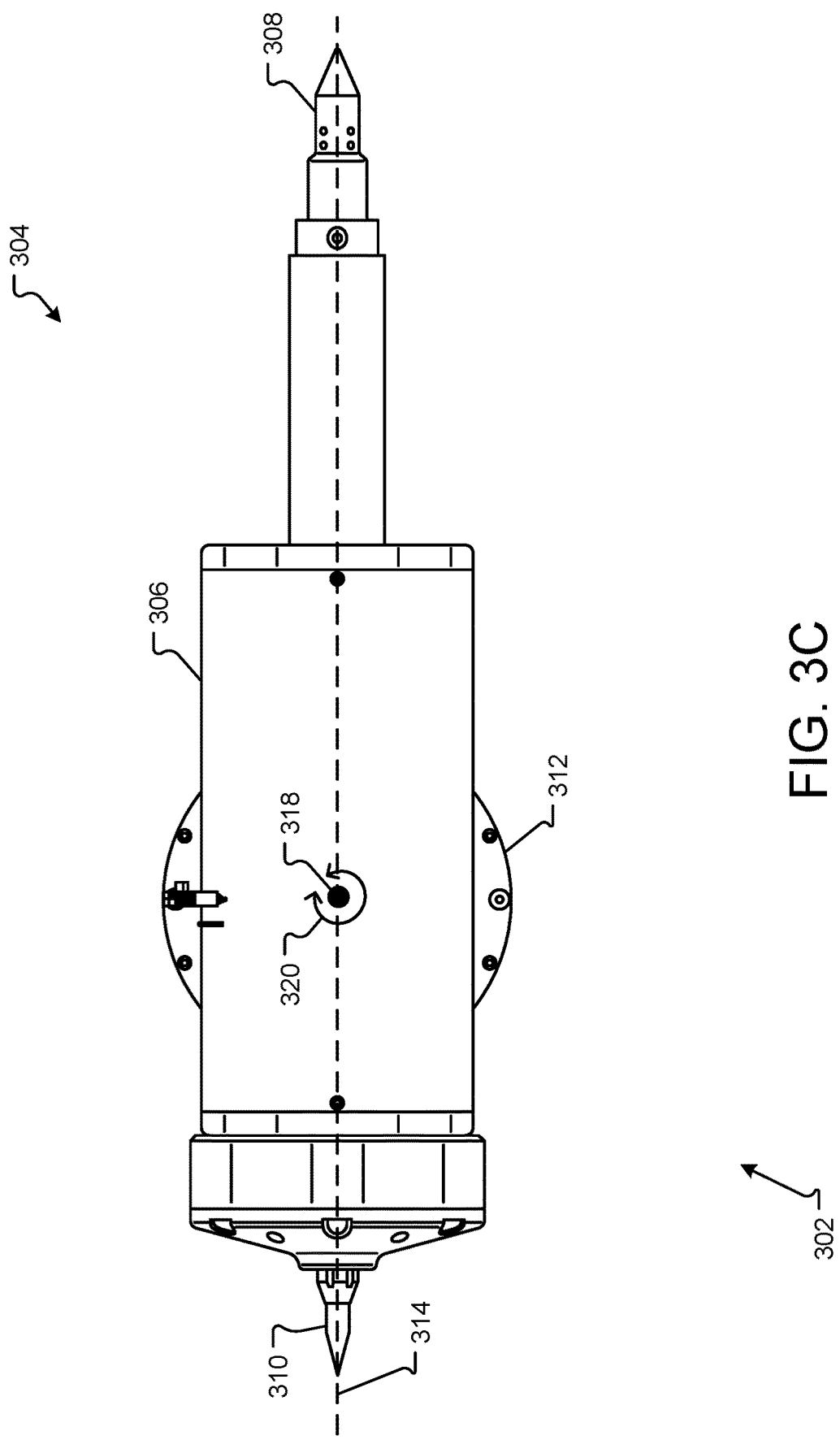
FIG. 3C is a top view diagram of the surgical tool according to at least one embodiment of the present disclosure.
Figure 3D:
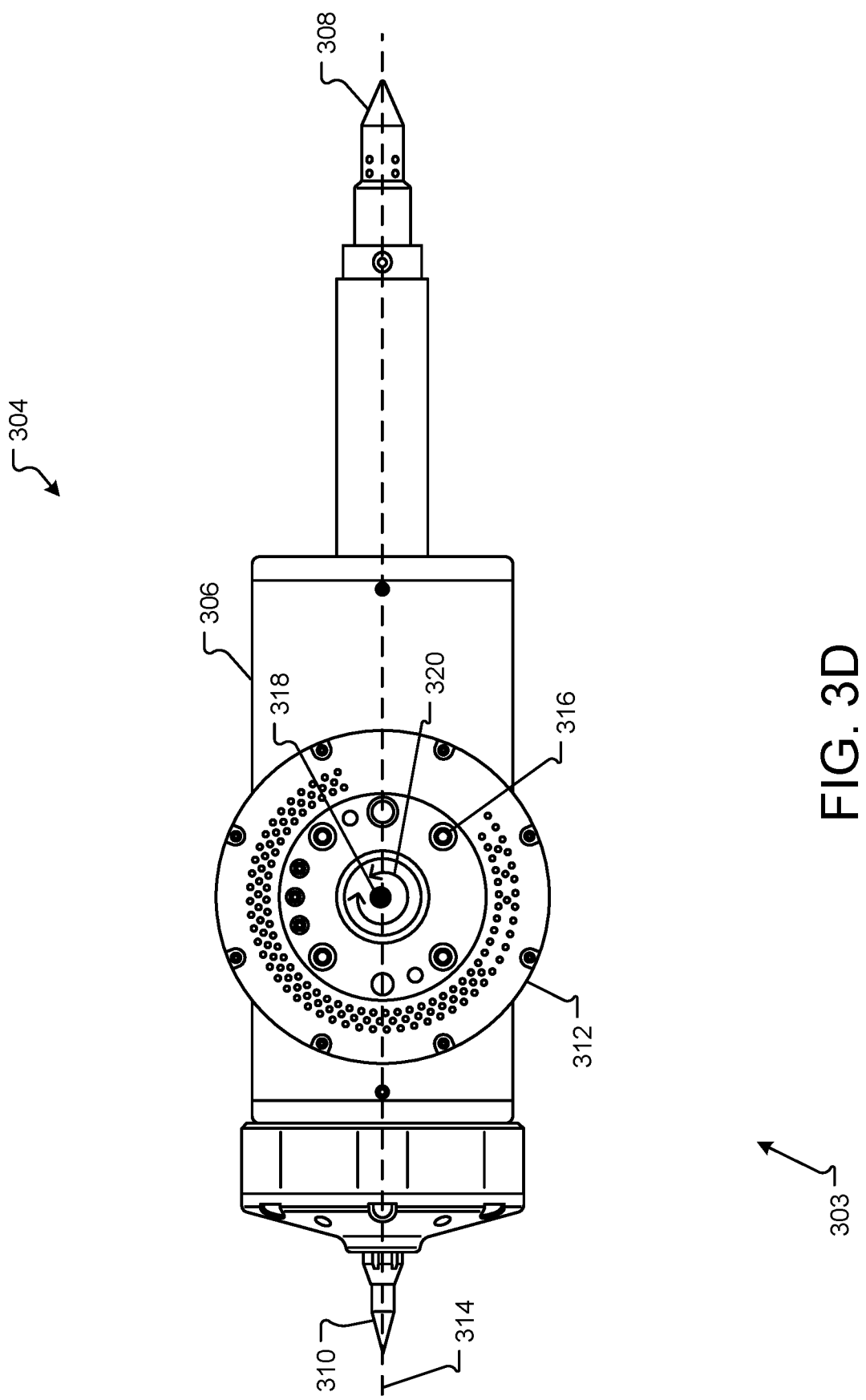
FIG. 3D is a bottom view diagram of the surgical tool according to at least one embodiment of the present disclosure.

FIG. 3C shows a top view diagram 302 of the surgical tool 304 according to at least one embodiment of the present disclosure, and FIG. 3D shows a bottom view diagram 303 of the surgical tool 304 according to at least one embodiment of the present disclosure. As shown in FIG. 3D, the robot mount flange 316 on the robot interface bracket 312 may include one or more kinematic coupling dimples that enable attachment of the surgical tool 304 to a distal end of a robot arm (e.g., a robot arm 116 of a robot 114 or a robotic surgical system by attaching to an end mount flange of the robot arm as described with reference to FIGS. 2A and 2B).

As described previously, the surgical tool 304 may be rotatable around the tool rotation axis 318 between the cutting position (e.g., disposing the blade support tip 308 in proximity to the target site) and the tissue pathway creation position (e.g., disposing the blunt tip end of the rod 310 in proximity to the target site). For example, as a non-limiting surgical operation example, the surgical tool 304 may first rotate to the cutting position to present the blade support tip 308 in proximity to the target site for creating an incision in the skin of a patient. Subsequently, the surgical tool 304 may rotate to the tissue pathway creation position (e.g., about the tool rotation axis 318) to present the blunt tip end of the rod 310 in proximity to the target site to create and/or dilate a tissue pathway to reach an internal site of the patient corresponding to the target site. The surgical tool 304 may then rotate between the cutting position to cut through additional tissue layers (e.g., fascia, fat, etc.) as needed and the tissue pathway creation position when those additional tissue layers are punctured until the internal site is reached and the surgical operation is finished (e.g., a screw is inserted, a cage is inserted, a drill is inserted, or an additional MIS tool is used/inserted).

Figure 4A:
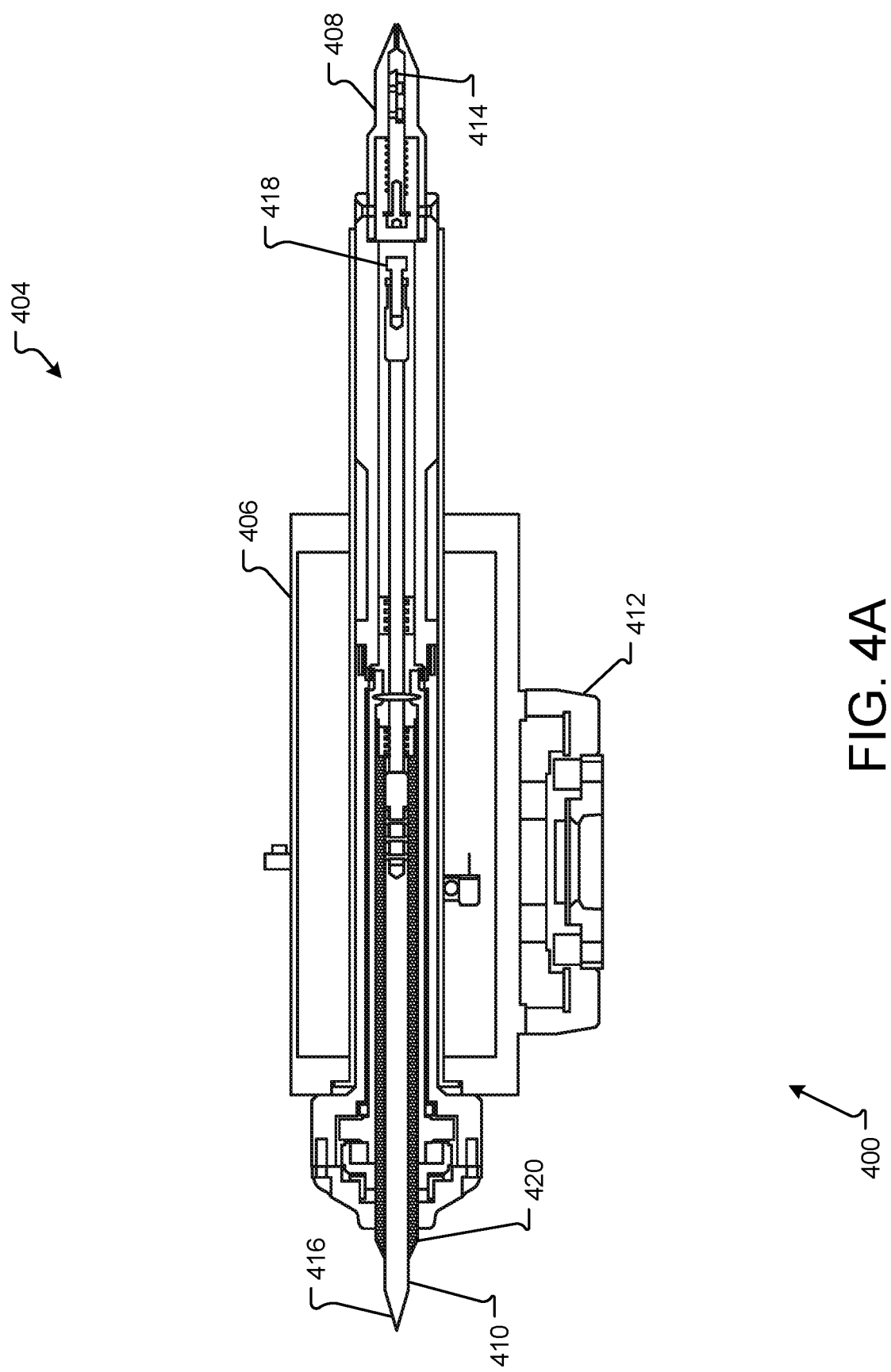
FIG. 4A is a detailed view of the side view diagram of the surgical tool according to at least one embodiment of the present disclosure.
Figure 4B:
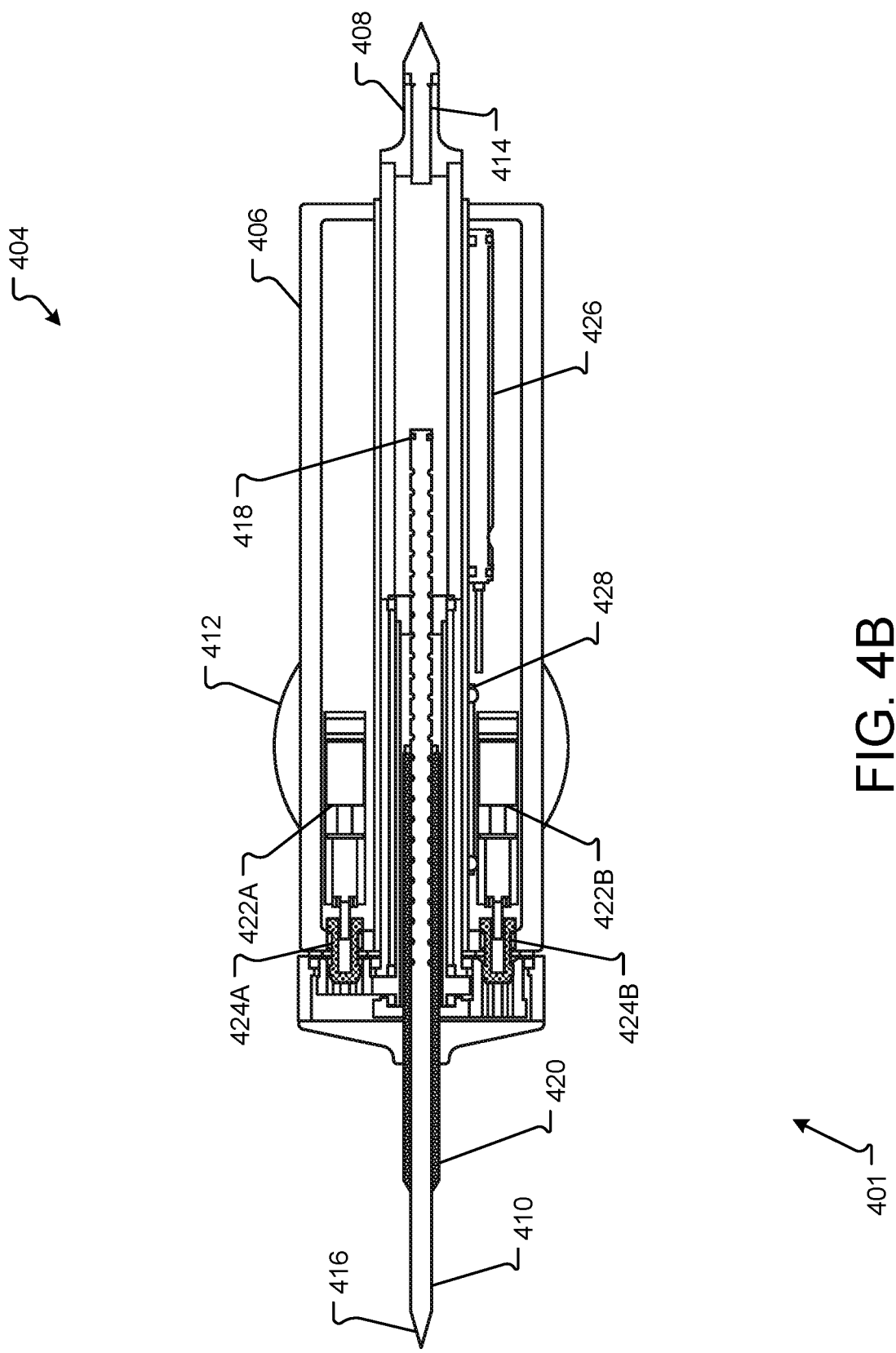
FIG. 4B is a detailed view of the top view diagram of the surgical tool according to at least one embodiment of the present disclosure.

FIG. 4A shows a detailed view 400 of a side view diagram of a surgical tool 404 (e.g., the side view diagram 301 of the surgical tool 304 as described with reference to FIG. 3B) according to at least one embodiment of the present disclosure, and FIG. 4B shows a detailed view 401 of a top view diagram of the surgical tool 404 (e.g., the top view diagram 302 of the surgical tool 304 as described with reference to FIG. 3C) according to at least one embodiment of the present disclosure. The surgical tool 402 may be an example of the surgical tool 304 as described with reference to FIGS. 3A-3D. For example, the surgical tool 404 may include a housing 406, a blade support tip 408 extending from a first end of the housing 406, a rod 410 (e.g., a trocar) that extends from a second end of the housing 406 in a direction away from the first end of the housing 406, and a robot interface bracket 412 that is coupled to the housing 406.

As mentioned previously with reference to FIG. 3A, a blade 414 may be disposed at least partially within the blade support tip 408, where the blade 414 includes a sharpened edge (e.g., for cutting through skin, fascia, fat, or other tissue layers). The blade 414 may be moveable between a retracted state where the sharpened edge is concealed within the blade support tip 408 and an extended state where the sharpened edge is exposed from the blade support tip 408. Additionally, the rod 410 may include a blunt tip end 416 and an actuation end 418. The surgical tool 404 may also include a tube 420 that is moved along the rod 410 (e.g., when the surgical tool 404 is in a tissue pathway creation position). The tube 420 may dilate a pathway from a target site of a patient to an internal point of the target site (e.g., for tissue pathway creation and/or dilation creation).

In some examples, the actuation end 418 is at least partially disposed within the housing 406, and the blunt tip end 416 extends from the second end of the housing 406 in a direction away from the first end of the housing 406 along a longitudinal axis that extends from the first end of the housing 406 to the second end of the housing 406 (e.g., the longitudinal axis 314 as described with reference to FIGS. 3A-3D).

As shown in FIG. 4B, extension of the blunt tip end 416 (e.g., and the tube 420) may be controlled by one or more motors 422. While a first motor 422A and a second motor 422B are shown in the example of FIG. 4B, a different number of motors 422 (e.g., fewer or greater than two (2)) can be used to control extension of the blunt tip end 416 (e.g., and the tube 420). For example, the motors 422 may be connected to corresponding rotary seal shafts 424 that can then connect to rotors which control extension or movement of the blunt tip end 416 (e.g., and the tube 420). Additionally, the surgical tool 404 may include one or more sensors disposed within the housing 406 that can be used for different purposes. For example, the surgical tool 404 may include a first stage encoder sensor 426 and a second stage encoder sensor 428 that are capable of performing depth sensing, axial force sensing, etc. Additionally or alternatively, the surgical tool 404 may include specific sensors for performing different sensing operations.

As will be described in more detail with reference to FIGS. 6 and 7A-7C, these sensors can be used for sensing a depth of insertion of the surgical tool 404 between the target site and an internal point of the target site. For example, the sensors can be used to control and sense the depth of insertion for the blade 414 disposed at least partially within the blade support tip 408 when the surgical tool 404 is in the cutting position, for the blunt tip end 416 of the rod 410 when the surgical tool 404 is in the tissue pathway creation position, or a combination thereof. The sensors (e.g., and any other necessary components, such as encoder magnets, static nuts, etc.) used for controlling and sensing the depth of insertion for either end of the surgical tool 404 may be referred to as a depth sensing subsystem disposed within the housing 406. In some examples, the depth sensing subsystem or additional encoder sensors disposed within the housing 406 may give additional information about the surgical tool 404 to assist in using the surgical tool 404, such as a position and a velocity of the surgical tool 404.

Additionally or alternatively, the sensors can be used for sensing a pressure exerted by the surgical tool 404, for sensing an amount of resistance encountered by the surgical tool 404, or a combination thereof. In some examples, the amount of resistance sensed by the sensors may indicate a presence of a certain tissue layer (e.g., fascia) that may require using the blade 414 to cut through, which may result in the surgical tool 404 rotating to the cutting position. The sensors (e.g., and any other necessary components) used for sensing a pressure exerted by the surgical tool 404 or for sensing an amount of resistance encountered by the surgical tool 404 may be referred to as a force sensing subsystem disposed within the housing 406.

Figure 5:
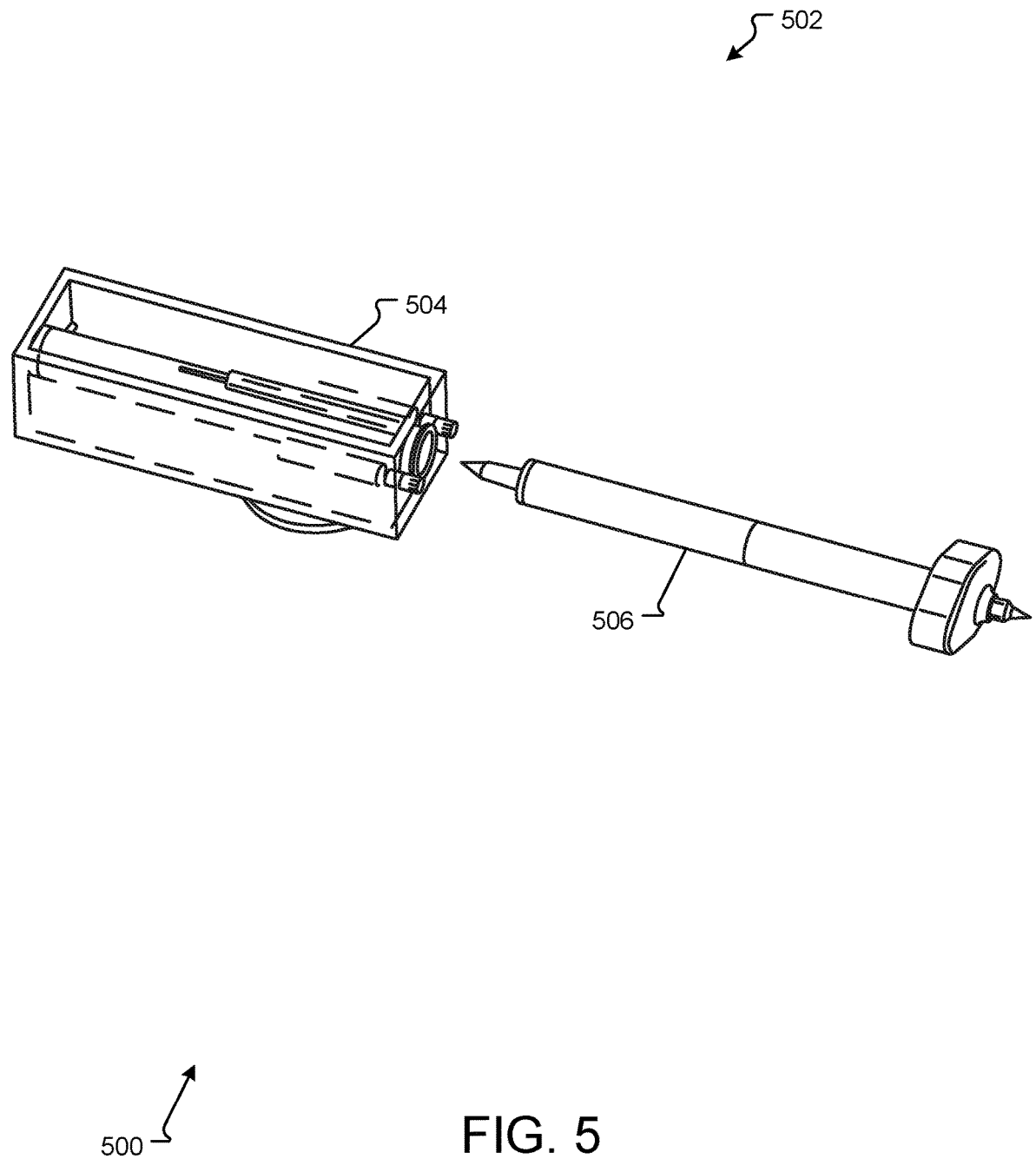
FIG. 5 is an assembly diagram for the surgical tool according to at least one embodiment of the present disclosure.

FIG. 5 shows an assembly diagram 500 for a surgical tool 502 according to at least one embodiment of the present disclosure. The surgical tool 502 may be an example of the surgical tool 304 and the surgical tool 404 as described with reference to FIGS. 3A-3D and FIGS. 4A-4B, respectively. In some examples, the surgical tool 502 may include a housing 504 and a combination unit 506. The combination unit 506 may include both a blade support tip (e.g., with a retractable blade) and a rod (e.g., with a blunt tip end or blunt tip trocar) as described herein. In some examples, the combination unit 506 may connect to the housing 504 via one or more rotary seal shafts that connect motors disposed in the housing 504 to rotors in the combination unit 506, where the rotors in the combination unit 506 control extension or movement of the blunt tip end of the rod. In some examples, the combination unit 506 (e.g., and the surgical tool 502 wholly) may be a sterilizable unit. Additionally or alternatively, the combination unit 506 may be disposable (e.g., after a surgical operation is completed, such that each combination unit 506 is sterilized when used for a given surgical operation).

Figure 6:
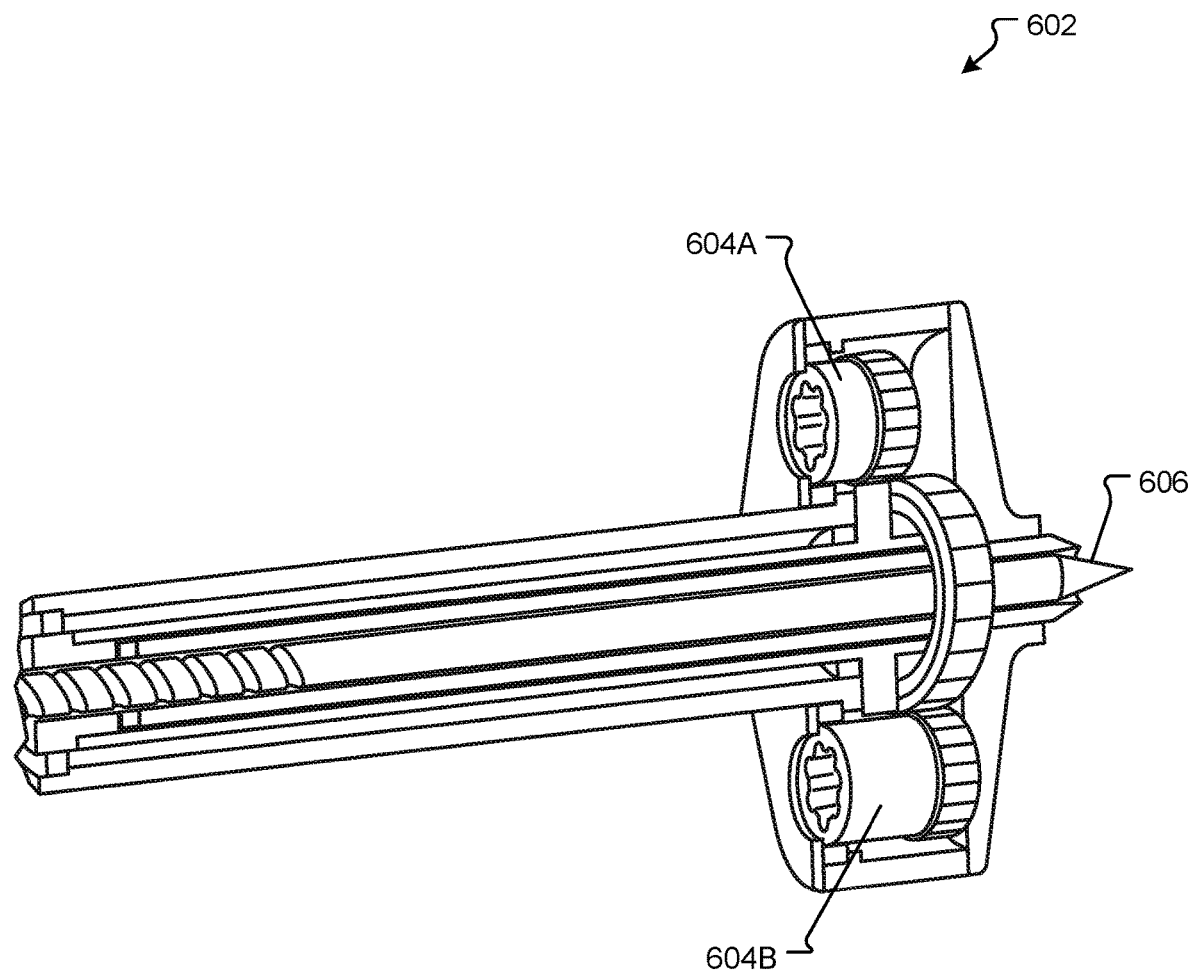
FIG. 6 is a perspective diagram of a blunt tip end of a rod of the surgical tool according to at least one embodiment of the present disclosure.

FIG. 6 shows a perspective diagram 600 of a blunt tip end of a rod of a surgical tool 602 according to at least one embodiment of the present disclosure. The surgical tool 602 may be an example of the surgical tool 304, the surgical tool 404, and the surgical tool 502 as described with reference to FIGS. 3A-3D, FIGS. 4A-4B, and FIG. 5, respectively. As described previously, the surgical tool 602 may include one or more motors disposed within a housing for the surgical tool 602 (e.g., the motors 422 as described with reference to FIG. 4B), where the one or more motors control extension of the blunt tip end of the rod from a second end of the housing in the direction away from a first end of the housing along a longitudinal axis. These motors disposed in the housing may connect to one or more rotors 604 (e.g., via rotary seal shafts in the housing) that control extension of the blunt tip end and/or a tube of the surgical tool 602 used for dilation. In some examples, a first rotor 604A may control extension of the blunt tip end, and a second rotor 604B may connect to an additional rotor 606 that controls extension of the tube for dilation. Additionally or alternatively, the first rotor 604A may control extension of the tube for dilation, and the second rotor 604B and additional rotor 606 may control extension of the bunt tip end. Additionally or alternatively, the rotors 604 and the additional rotor 606 may all work together to control extension of the blunt tip end and/or the tube. Operation and actuation of the blunt tip end and/or the tube extending for the surgical tool 602 are described in greater detail with reference to FIGS. 7A-7C.

Figure 7A:
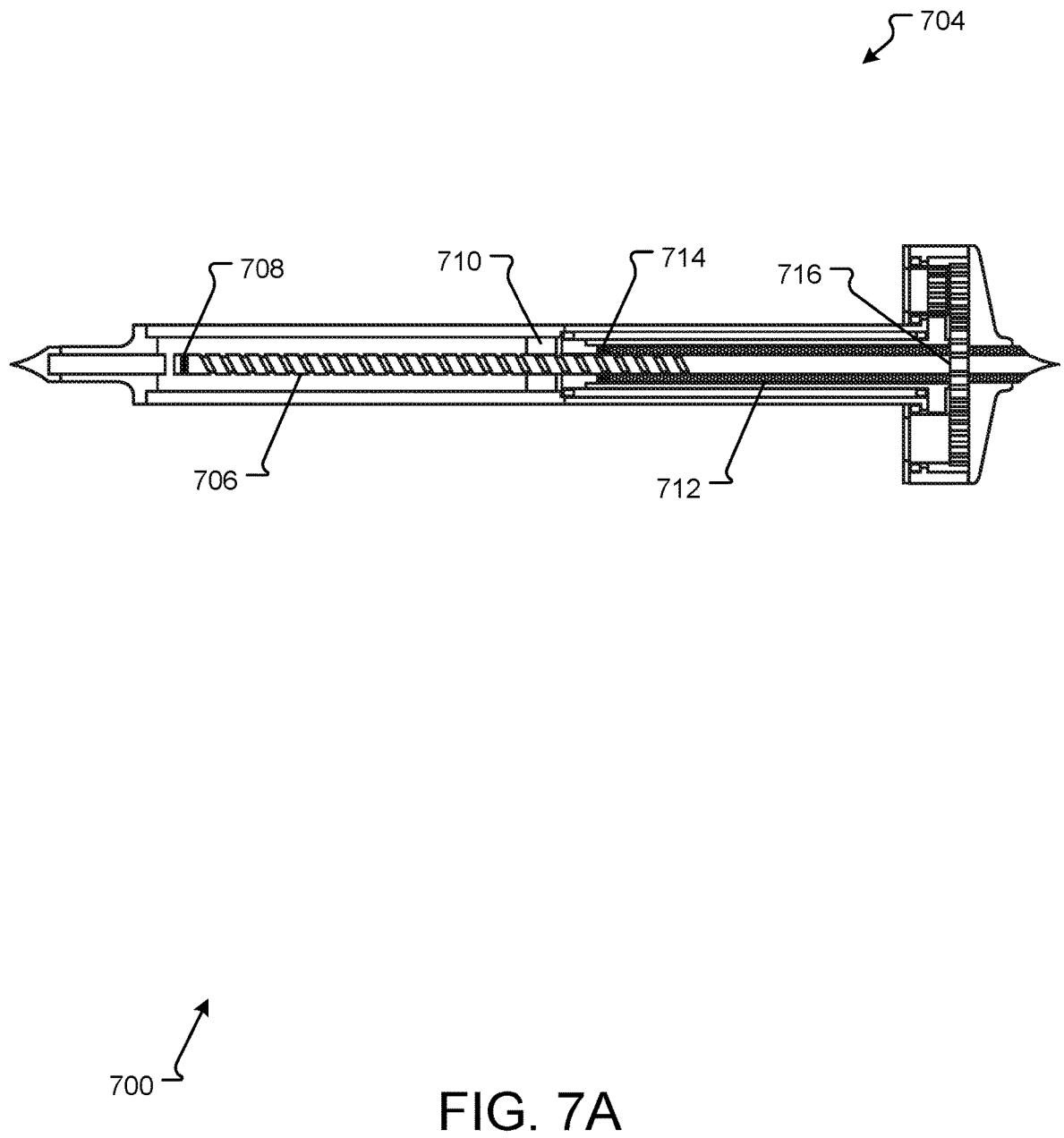
FIGS. 7A-7C are diagrams of actuation of the blunt tip end of the rod of the surgical tool according to at least one embodiment of the present disclosure.
Figure 7B:
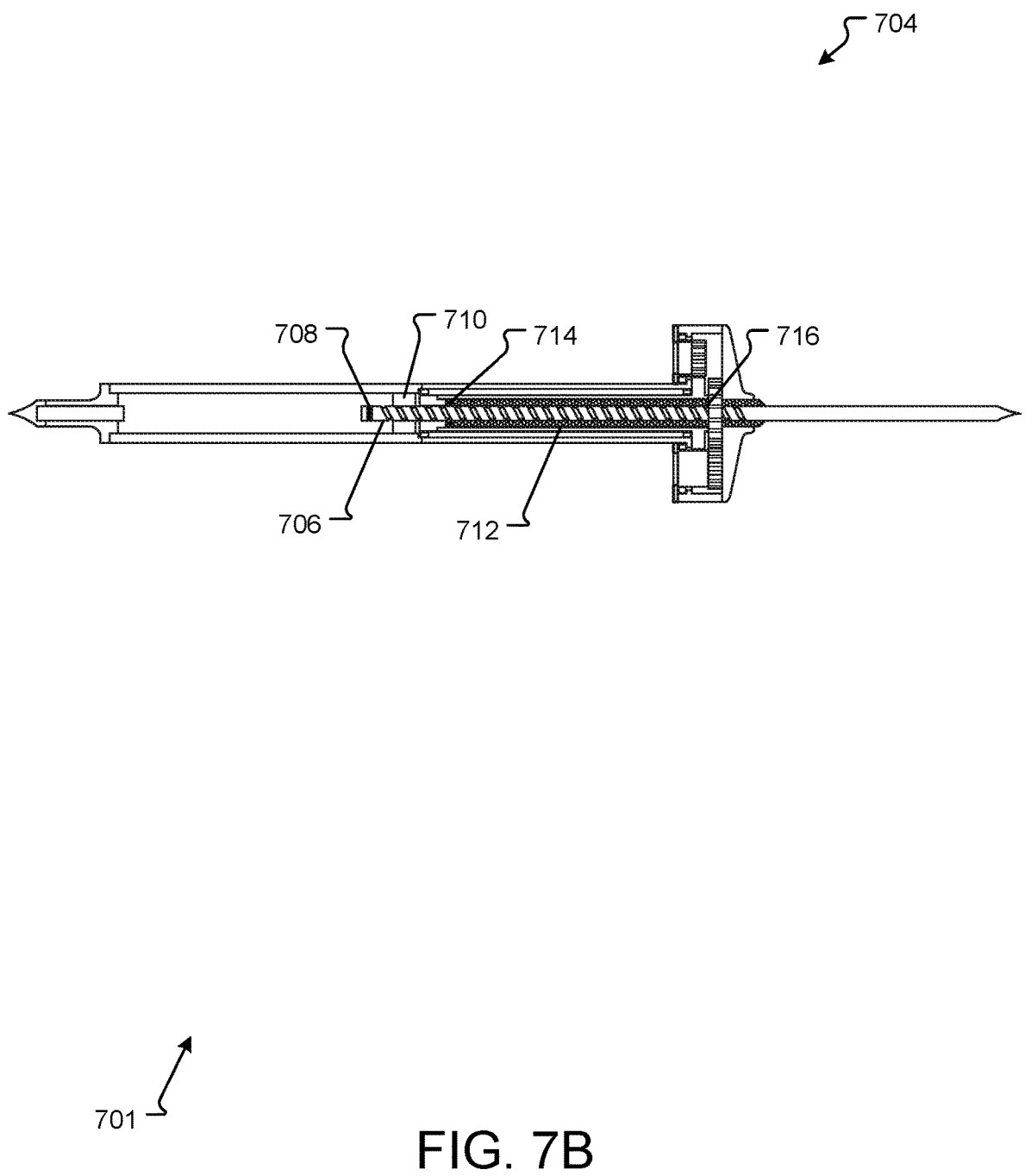
Figure 7C:
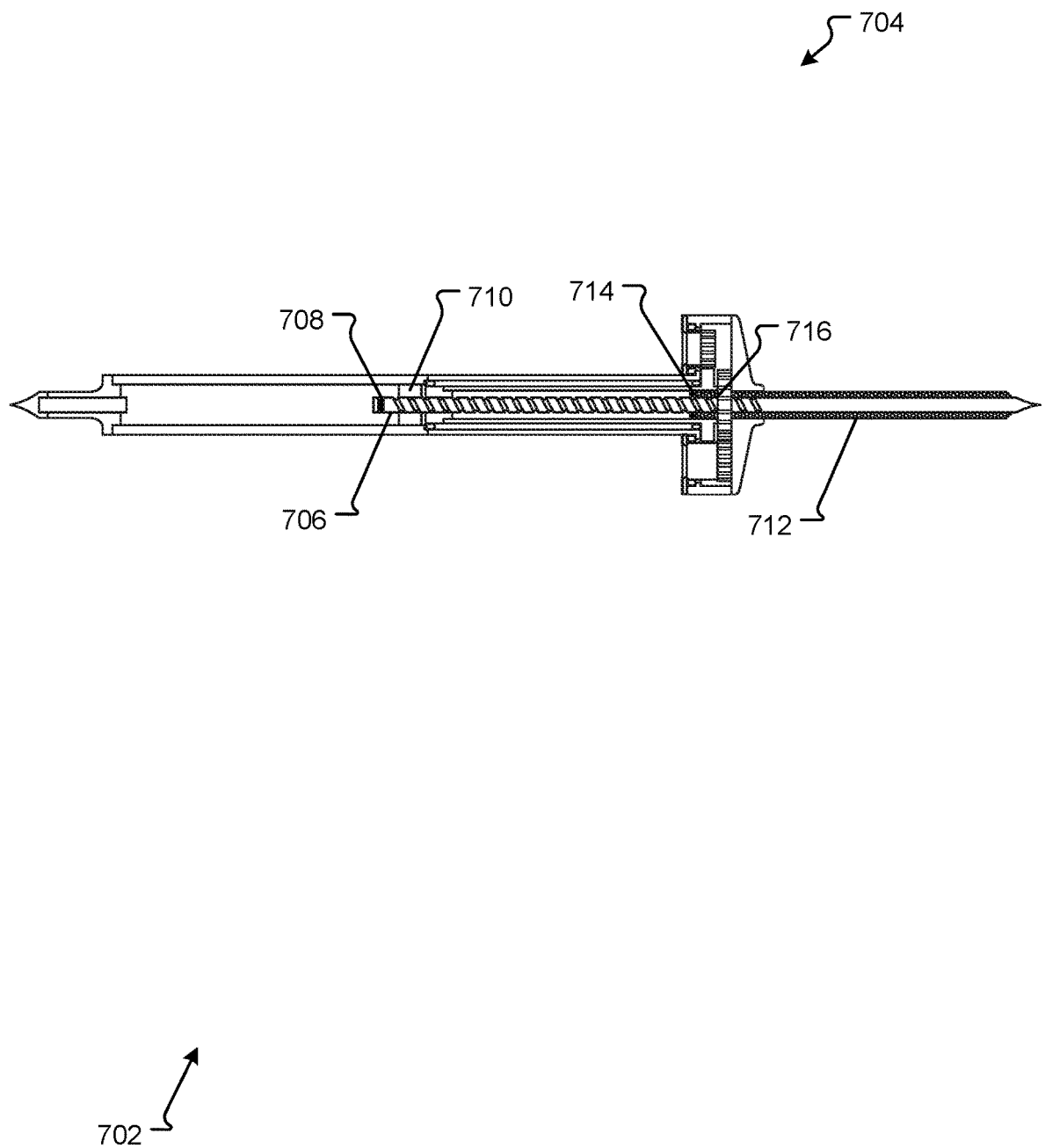

FIGS. 7A-7C show diagrams 700, 701, and 702, respectively, of actuation of a blunt tip end of a rod 706 of a surgical tool 704 according to at least one embodiment of the present disclosure. The surgical tool 704 may be an example of the surgical tool 304, the surgical tool 404, the surgical tool 502, and the surgical tool 602 as described with reference to FIGS. 3A-3D, FIGS. 4A-4B, FIG. 5, and FIG. 6, respectively. In particular, the surgical tool 704 shown in the examples of FIGS. 7A-7C may represent a combination unit that includes both a blade support tip (e.g., with a retractable blade) and the rod 706 (e.g., with a blunt tip end and an actuation end) as described with reference to FIGS. 5 and 6 (e.g., the combination unit 506).

As described previously, the blunt tip end of the rod 706 and a tube 712 that is moved along the rod may extend out from the surgical tool 704 for tissue pathway creation and/or dilation creation. The extension of these components may be controlled by a depth sensing subsystem disposed within the housing for the surgical tool 704. For example, the depth sensing subsystem may include a first stage encoder magnet 708, a first stage static nut 710, a second stage encoder magnet 714, and a second stage static nut 716. In some examples, the first stage encoder magnet 708 and the first stage static nut 710 may control extension of the rod 706, and the second stage encoder magnet 714 and the second stage static nut 716 may control extension of the tube 712. Additionally or alternatively, the first stage encoder magnet 708, the first stage static nut 710, the second stage encoder magnet 714, and the second stage static nut 716 may work together to control extension of the rod 706, the tube 712, or both. In some examples, the depth sensing subsystem (e.g., or additional encoder sensors, nuts, magnets, etc. of the surgical tool 704) may give additional information about the surgical tool 704, such as a position and a velocity of the surgical tool 404 while the surgical tool 704 is in use.

FIG. 7A shows both the rod 706 and the tube 712 in an unextended or minimally extended position, where the first stage encoder magnet 708 is far from the first stage static nut 710 and the second stage encoder magnet 714 is far from the second stage static nut 716. FIG. 7B shows the rod 706 at an extended position with the first stage encoder magnet 708 being close to the first stage static nut 710 and the tube 712 at an unextended or minimally extended position with the second stage encoder magnet 714 being far from the second stage static nut 716. FIG. 7C shows the rod 706 and the tube 712 being in extended positions, where the first stage encoder magnet 708 is close to the first stage static nut 710 and the second stage encoder magnet 714 is close to the second stage static nut 716. In some examples, the first stage encoder magnet 708, the first stage static nut 710, the second stage encoder magnet 714, and the second stage static nut 716 may work in combination with one or more sensors disposed in the housing for the surgical tool 704 (e.g., the sensors 426 and 428 as described with reference to FIG. 4B) to control extension of the rod 706 and/or the tube 712.

Figure 8:
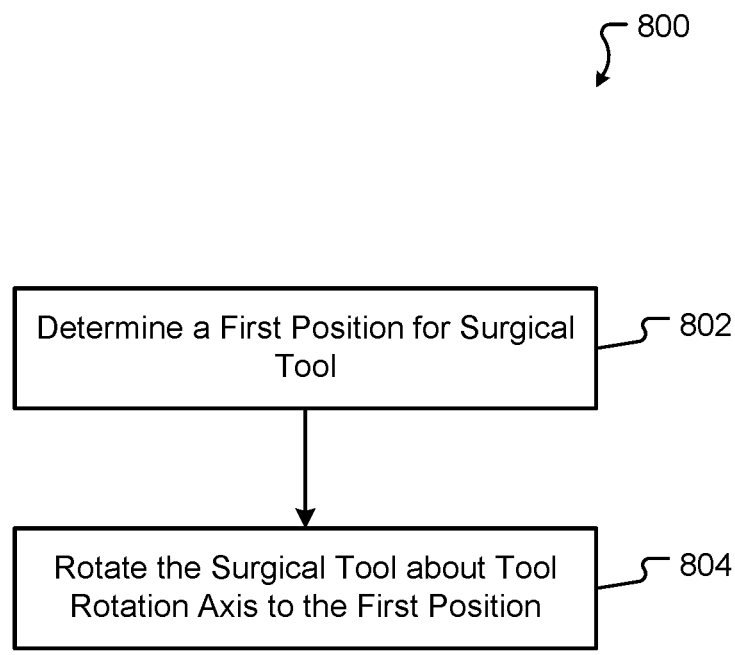
FIG. 8 is a flowchart of a method for operating a robotic surgical system according to at least one embodiment of the present disclosure.

FIG. 8 depicts a method 800 that may be used, for example, to operate the surgical tool as described herein for positioning a given end of the surgical tool in proximity to a target site of a patient. The method 800 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 800. The at least one processor may perform the method 800 by executing elements stored in a memory such as the memory 106. The elements stored in the memory and executed by the processor may cause the processor to execute one or more steps of a function as shown in method 800. One or more portions of a method 800 may be performed by the processor executing any of the contents of memory, such as an image processing 120, a segmentation 122, a transformation 124, and/or a registration 128.

The method 800 comprises determining a first position for a surgical tool, where the first position can be a cutting position that disposes a blade support tip in proximity to a target site or a tissue pathway creation position that disposes a blunt tip end in proximity to the target site (step 802). For example, the surgical tool may be rotatable between the cutting position and the tissue pathway creation position about a tool rotation axis (e.g., as described with reference to FIGS. 3A-3D). In some examples, the surgical tool may determine the first position or a person operating the surgical tool (e.g., physician, surgeon, medical professional, etc.) may determine the first position based on a determined operation for the surgical tool to perform. For example, the first position for the surgical tool may be the cutting position when making an initial incision, for cutting through other tissue layers (e.g., fascia, fat, etc.) based on measurements gathered by subsystems of the surgical tool (e.g., an amount of pressure determined by a force sensing subsystem). Additionally or alternatively, the first position for the surgical tool may be the tissue pathway creation position after an incision is made to create a tissue pathway and/or a dilation to reach an internal point of a patient (e.g., of a target site).

The method 800 also comprises rotating the surgical tool about the tool rotation axis to the first position (step 804). In some examples, if the first position is the cutting position, a blade disposed within the blade support tip may be extended from a retracted state within the blade support tip to provide a sharpened edge for performing a cutting procedure. Additionally or alternatively, if the second position is the tissue pathway creation position, the blunt tip end may be extended from the surgical tool to create a tissue pathway and/or dilation. In some examples, sensors and/or other components (e.g., of a depth sensing subsystem of the surgical tool) may sense and control how far to extend a corresponding part of the surgical tool (e.g., control and sense a depth of insertion for the blade when in the cutting position, for the blunt tip end of the rod when in the tissue pathway creation position, or a combination thereof). Additionally, one or more motors may control extension and/or a velocity of the different components and/or rotation of the surgical tool.

By having the surgical tool be capable of rotating between the different positions, a person operating a robotic surgical system that includes the surgical tool does not need to replace surgical tools that are designed for each operation specifically. For example, in some cases, a first tool is used for cutting, and a second tool is used for tissue pathway creation and/or dilation creation. Accordingly, a person may have to switch between the first tool and the second tool to perform a surgical operation, which would increase a time of the surgical operation. With the surgical tool described herein, cutting, tissue pathway creation, and/or dilation creation can all be performed with a single tool, thereby decreasing an amount of time needed to perform a corresponding surgical operation. Additionally, the surgical tool described herein may lessen a chance of harming the patient (e.g., by controlling the pressure exerted by a given end of the surgical tool, controlling a length of incisions made by the blade, etc.).

The present disclosure encompasses embodiments of the method 800 that comprise more or fewer steps than those described above, and/or one or more steps that are different than the steps described above.

As noted above, the present disclosure encompasses methods with fewer than all of the steps identified in FIG. 8 (and the corresponding description of the method 800), as well as methods that include additional steps beyond those identified in FIG. 8 (and the corresponding description of the method 800). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A robotic surgical system, comprising:
    a robot arm comprising a proximal end and a distal end; and
    a surgical tool, comprising:
        a housing comprising a longitudinal axis extending from a first end of the housing to a second end of the housing;
        a blade support tip extending from the first end of the housing in a direction away from the second end of the housing along the longitudinal axis;
        a blade disposed at least partially within the blade support tip, the blade comprising a sharpened edge;
        a rod comprising a blunt tip end and an actuation end, wherein the actuation end is disposed within the housing, and wherein the blunt tip end extends from the second end of the housing in a direction away from the first end of the housing along the longitudinal axis; and
        a robot interface bracket coupled to the housing, the robot interface bracket comprising a robot mount flange comprising a tool rotation axis arranged perpendicular to the longitudinal axis, wherein the surgical tool is attached to the distal end of the robot arm via the robot mount flange, wherein the surgical tool is rotatable about the tool rotation axis between a cutting position disposing the blade support tip in proximity to a target site and a tissue pathway creation position disposing the blunt tip end in proximity to the target site, wherein the blade is moveable between a retracted state where the sharpened edge is concealed within the blade support tip and an extended state where the sharpened edge is exposed from the blade support tip.

2. The robotic surgical system of claim 1, further comprising:
    a tube that is moved along the rod when the surgical tool is in the tissue pathway creation position, wherein the tube dilates a pathway from the target site to an internal point of the target site.

3. The robotic surgical system of claim 1, further comprising:
    one or more motors disposed within the housing that control extension of the blunt tip end of the rod from the second end of the housing in the direction away from the first end of the housing along the longitudinal axis.

4. The robotic surgical system of claim 1, further comprising:
    a depth sensing subsystem disposed within the housing, the depth sensing subsystem comprising one or more encoder sensors that indicate one or more characteristics of the surgical tool.

5. The robotic surgical system of claim 4, wherein the depth sensing subsystem is used to control and sense the depth of insertion for the blade disposed at least partially within the blade support tip in the cutting position, for the blunt tip end of the rod in the tissue pathway creation position, or a combination thereof.

6. The robotic surgical system of claim 4, wherein the depth sensing subsystem further comprises one or more encoder magnets, one or more static nuts, or a combination thereof for sensing the depth of insertion of the surgical tool.

7. The robotic surgical system of claim 4, wherein the one or more characteristics of the surgical tool indicated by the one or more encoder sensors comprise a depth of insertion of the surgical tool between the target site and an internal point of the target site, a position of the surgical tool, a velocity of the surgical tool, or a combination thereof.

8. The robotic surgical system of claim 1, further comprising:
    an axial force sensing subsystem disposed within the housing, the axial force sensing subsystem comprising one or more force sensors for sensing a pressure exerted by the surgical tool, for sensing an amount of resistance encountered by the surgical tool, or a combination thereof.

9. The robotic surgical system of claim 8, wherein the amount of resistance sensed by the axial force sensing subsystem indicates a presence of a tissue layer.

10. The robotic surgical system of claim 1, wherein the surgical tool comprises a sterilizable unit.

11. A surgical tool, comprising:
a housing comprising a longitudinal axis extending from a first end of the housing to a second end of the housing;
a blade support tip extending from the first end of the housing in a direction away from the second end of the housing along the longitudinal axis;
a blade disposed at least partially within the blade support tip, the blade comprising a sharpened edge;
a rod comprising a blunt tip end and an actuation end, wherein the actuation end is disposed within the housing, and wherein the blunt tip end extends from the second end of the housing in a direction away from the first end of the housing along the longitudinal axis;
a robot interface bracket coupled to the housing, the robot interface bracket comprising a robot mount flange comprising a tool rotation axis arranged perpendicular to the longitudinal axis, wherein the housing is attachable to a distal end of a robot arm via the robot mount flange, wherein the surgical tool is rotatable about the tool rotation axis between a cutting position disposing the blade support tip in proximity to a target site and a tissue pathway creation position disposing the blunt tip end in proximity to the target site; and
a tube that is moved along the rod when the surgical tool is in the tissue pathway creation position, wherein the tube dilates a pathway from the target site to an internal point of the target site.

12. The surgical tool of claim 11, wherein the blade is moveable between a retracted state where the sharpened edge is concealed within the blade support tip and an extended state where the sharpened edge is exposed from the blade support tip.

13. The surgical tool of claim 11, further comprising:
one or more motors disposed within the housing that control extension of the blunt tip end of the rod from the second end of the housing in the direction away from the first end of the housing along the longitudinal axis.

14. The surgical tool of claim 11, further comprising:
a depth sensing subsystem disposed within the housing, the depth sensing subsystem comprising one or more encoder sensors that indicate one or more characteristics of the surgical tool.

15. The surgical tool of claim 14, wherein the depth sensing subsystem is used to control and sense the depth of insertion for the blade disposed at least partially within the blade support tip in the cutting position, for the blunt tip end of the rod in the tissue pathway creation position, or a combination thereof.

16. The surgical tool of claim 14, wherein the depth sensing subsystem further comprises one or more encoder magnets, one or more static nuts, or a combination thereof for sensing the depth of insertion of the surgical tool.

17. The surgical tool of claim 11, further comprising:
an axial force sensing subsystem disposed within the housing, the axial force sensing subsystem comprising one or more force sensors for sensing a pressure exerted by the surgical tool, for sensing an amount of resistance encountered by the surgical tool, or a combination thereof.

18. A system, comprising:
a surgical robot comprising:
a robot arm comprising a proximal end and a distal end; and
a surgical tool, comprising:
a housing comprising a longitudinal axis extending from a first end of the housing to a second end of the housing;
a blade support tip extending from the first end of the housing in a direction away from the second end of the housing along the longitudinal axis;
a blade disposed at least partially within the blade support tip, the blade comprising a sharpened edge;
a rod comprising a blunt tip end and an actuation end, wherein the actuation end is disposed within the housing, and wherein the blunt tip end extends from the second end of the housing in a direction away from the first end of the housing along the longitudinal axis;
one or more motors disposed within the housing that control extension of the blunt tip end of the rod from the second end of the housing in the direction away from the first end of the housing along the longitudinal axis; and
a robot interface bracket coupled to the housing, the robot interface bracket comprising a robot mount flange comprising a tool rotation axis arranged perpendicular to the longitudinal axis, wherein the surgical tool is attached to the distal end of the robot arm via the robot mount flange, and wherein the surgical tool is rotatable about the tool rotation axis between a cutting position disposing the blade support tip in proximity to a target site and a tissue pathway creation position disposing the blunt tip end in proximity to the target site.

19. The system of claim 18, wherein the blade is moveable between a retracted state where the sharpened edge is concealed within the blade support tip and an extended state where the sharpened edge is exposed from the blade support tip.

20. The system of claim 18, further comprising:
a processor coupled with the surgical robot; and
a memory coupled with and readable by the processor and storing therein instructions that, when executed by the processor, cause the processor to:
determine a first position for the surgical tool as the cutting position or the tissue pathway creation position; and
rotate the surgical tool about the tool rotation axis to the first position.

* * * * *